US011427559B2

(12) United States Patent
Zhang

(10) Patent No.: US 11,427,559 B2
(45) Date of Patent: Aug. 30, 2022

(54) SUBSTITUTED QUINOLINES USEFUL AS KINASE INHIBITORS

(71) Applicant: Dawei Zhang, Thousand Oaks, CA (US)

(72) Inventor: Dawei Zhang, Thousand Oaks, CA (US)

(73) Assignee: Teligene Ltd., Suzhou (CN)

( * ) Notice: Subject to any disclaimer, the term of this patent is extended or adjusted under 35 U.S.C. 154(b) by 147 days.

(21) Appl. No.: 16/970,349

(22) PCT Filed: Feb. 20, 2019

(86) PCT No.: PCT/US2019/018841
§ 371 (c)(1),
(2) Date: Aug. 15, 2020

(87) PCT Pub. No.: WO2019/165003
PCT Pub. Date: Aug. 29, 2019

(65) Prior Publication Data
US 2021/0087166 A1 Mar. 25, 2021

Related U.S. Application Data

(60) Provisional application No. 62/710,503, filed on Feb. 20, 2018.

(51) Int. Cl.
*C07D 401/12* (2006.01)
*A61P 35/00* (2006.01)

(52) U.S. Cl.
CPC ............ *C07D 401/12* (2013.01); *A61P 35/00* (2018.01)

(58) Field of Classification Search
CPC .................................................. C07D 401/12
See application file for complete search history.

(56) References Cited

U.S. PATENT DOCUMENTS

| 7,501,516 | B2 | 3/2009 | Hennequin |
| 2012/0101116 | A1 | 4/2012 | Zhang |
| 2015/0126537 | A1 | 5/2015 | Zhang |

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*

* cited by examiner

*Primary Examiner* — Shawquia Jackson
(74) *Attorney, Agent, or Firm* — Feng Tian

(57) ABSTRACT

The present invention is directed to novel quinoline-3-carbonitriles according to Formula I, their derivatives, pharmaceutically acceptable salts, solvates and hydrates thereof. The compounds and compositions of the present invention have protein kinases inhibitory activities and are useful for the treatment of protein kinases mediated diseases and conditions.

14 Claims, No Drawings

SUBSTITUTED QUINOLINES USEFUL AS KINASE INHIBITORS

CROSS REFERENCE

This invention claims the benefit of U.S. Provisional Patent Application No. 62/710,503, filed on Feb. 20, 2018, which is hereby incorporated herein by reference in its entirety.

FIELD OF THE INVENTION

The present invention generally relates to inhibitors of kinase and pharmaceutically acceptable salts, solvates, hydrates, prodrugs and metabolites thereof, the preparation thereof, and the use of such compounds or compositions thereof to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. For example, protein tyrosine kinases (PTKs) are enzymes, which catalyze the phosphorylation of specific tyrosine residues in cellular proteins. Examples of kinases in the protein kinase family include, without limitation, Abl1 (v-Abl Abelson murine leukemia viral oncogene homolog 1), Akt, Alk, Bcr-Abl1, Blk, Brk, Btk, c-Kit, c-Met, c-Src, c-Fms, CDK1-10, b-Raf, c-Raf1, CSF1R, CSK, EGFR, ErbB2, ErbB3, ErbB4, Erk, FGFR1, FGFR2, FGFR3, FGFR4, FGFR5, Flt-1, Fps, Frk, Jak, KDR, MEK, PDGFR, PIK, PKC, PYK2, Ros, Tie, Tie2, and Zap70. Due to their activity in numerous cellular processes, protein kinases have emerged as important therapeutic targets.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy. The human epidermal growth factor receptor (HER) tyrosine kinase family consists of four structurally related cellular receptors: the epidermal growth factor receptor (EGFR;HER1), HER2 (ErbB2), HER3 (ErbB3), and HER4. Quinazolines are a known class of kinase inhibitors with utility for the treatment of cancer, angiogenesis disorders, and inflammatory disorders. To this end, attempts have been made to identify small molecules which act as protein kinase inhibitors. For example, quinazoline derivatives (PCT WO 00177104; US20050250761; WO2004069791) have been described as HER kinase inhibitors.

EGFR inhibitors erlotinib and gefitinib as well as the dual EGFR/HER2 inhibitor lapatinib are FDA-approved cancer drugs that are effective against multiple solid tumor cancers. However, their effectiveness is also limited by the drug resistance that frequent emerges following treatment point mutations in the kinase domain of EGFR as well as upregulation of by-pass signaling pathways are frequently observed resistance mechanisms in patients treated with gefitinib and erlotinib.

Thus, the compounds that can inhibit resistant mutant protein kinases activity with improved efficacy or overcoming drug resistance are highly desired.

SUMMARY OF THE INVENTION

In some embodiments of the present invention, there are provided compounds of Formula I:

I or a pharmaceutically acceptable salt, solvate, prodrug, stereoisomer, tautomer or metabolite thereof, wherein $R^1$ is independently hydrogen, $C_1$-$C_6$ alkyl, $C_1$-$C_6$ alkynyl, $C_1$-$C_6$ alkoxy, F, Cl, CN, or $CF_3$;

$R^2$ is hydrogen, $C_1$-$C_6$ alkyl, or $OR^4$;

$R^3$ is hydrogen, —$CH_2NR^8R^9$, or —$(CHR^{10})_tR^{11}$;

$R^4$ is $C_1$-$C_6$ alkyl, —$CR^6R^7(CR^6R^7)_qOR^5$, tetrahydrofuran-3-yl, —$(CH_2)_t$-morpholine, —$(CH_2)_t$-piperidine, or —$(CH_2)_t$-piperazine-N($C_1$-$C_3$ alkyl);

each $R^5$, $R^6$, and $R^7$ is independently hydrogen, $C_1$-$C_6$ alkyl, $C_6$-$C_{12}$ aryl, 5-12 membered heteroaryl, $C_3$-$C_{12}$ cycloalkyl or 3-12 membered heteroalicyclic; or any two of $R^5$, $R^6$, and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^5$, $R^6$, and $R^7$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;

$R^8$ and $R^9$ are independently hydrogen, $C_1$-$C_6$ alkyl, or $CR^6R^7(CR^6R^7)_qOR^5$;

each $R^{10}$ is independently hydrogen or $C_1$-$C_6$ alkyl;

$R^{11}$ is morpholine, piperidine, piperazine, piperazine-N ($C_1$-$C_6$ alkyl), or pyrrolidine, and each hydrogen in $R^{11}$ is optionally substituted by one or more $C_1$-$C_6$ alkyl, $C_1$-$C_6$ alkoxy, halogen, OH, $NH_2$, NH($C_1$-$C_6$ alkyl), or N($C_1$-$C_6$ alkyl)$_2$;

Y is Oxygen or Nitrogen;

each m is independently 0 or 1;

each n is independently 1 or 2;

each p is independently 0, 1, 2, 3, 4, or 5;

each t is independently 1, 2, or 3; and each q is independently 0, 1, 2, 3, or 4.

The present invention further provides pharmaceutical compositions comprising a compound of Formula I described above and a pharmaceutically acceptable carrier.

The present invention further provides methods for regulating the kinase signaling transduction comprising administrating to a mammalian subject a therapeutically effective amount of any of the compounds of Formula I described above or compounds disclosed herein.

DETAILED DESCRIPTION OF THE INVENTION

In some embodiments of the present invention, there are provided compounds of Formula I:

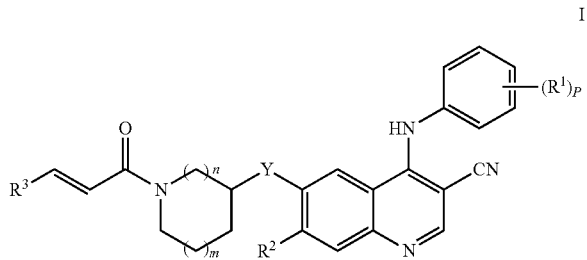

I or a pharmaceutically acceptable salt, solvate, prodrug, stereoisomer, tautomer or metabolite thereof, wherein
- $R^1$ is independently hydrogen, $C_1$-$C_6$ alkyl, $C_1$-$C_6$ alkynyl, $C_1$-$C_6$ alkoxy, F, Cl, CN, or $CF_3$;
- $R^2$ is hydrogen, $C_1$-$C_6$ alkyl, or $OR^4$;
- $R^3$ is hydrogen, —$CH_2NR^8R^9$, or —$(CHR^{10})_rR^{11}$;
- $R^4$ is $C_1$-$C_6$ alkyl, —$CR^6R^7(CR^6R^7)_qOR^5$, tetrahydrofuran-3-yl, —$(CH_2)_t$-morpholine, —$(CH_2)_t$-piperidine, or —$(CH_2)_t$-piperazine-N($C_1$-$C_3$ alkyl);
- each $R^5$, $R^6$, and $R^7$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^5$, $R^6$, and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^5$, $R^6$, and $R^7$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;
- $R^8$ and $R^9$ are independently hydrogen, $C_1$-$C_6$ alkyl, or $CR^6R^7(CR^6R^7)OR^5$;
- each $R^{10}$ is independently hydrogen or $C_1$-$C_6$ alkyl;
- $R^{11}$ is morpholine, piperidine, piperazine, piperazine-N($C_1$-$C_6$ alkyl), or pyrrolidine,
- and each hydrogen in $R^{11}$ is optionally substituted by one or more $C_1$-$C_6$ alkyl, $C_1$-$C_6$ alkoxy, halogen, OH, $NH_2$, $NH(C_1$-$C_6$ alkyl), or $N(C_1$-$C_6$ alkyl)$_2$;
- Y is Oxygen or Nitrogen;
- each m is independently 0, or 1;
- each n is independently 1, or 2;
- each p is independently 0, 1, 2, 3, 4, or 5;
- each t is independently 1, 2, or 3; and each q is independently 0, 1, 2, 3, or 4.

In certain embodiments, the invention provides for compounds of Formula I wherein $R^1$ is hydrogen, F or Cl. In other embodiments, the invention provides for compounds of Formula I wherein $R^2$ is —OEt. In some embodiments, the invention provides for compounds of Formula I wherein $R^2$ is —OMe. In other embodiments, the invention provides for compounds of Formula I wherein $R^3$ is H or —$CH_2N(CH_3)_2$. In some embodiments, the invention provides for compounds of Formula I wherein $R^2$ is $OR4$. In some embodiments, the invention provides for compounds of Formula I wherein $R^2$ is OEt or OMe. In some embodiments, the invention provides for compounds of Formula I wherein n is 2 and m is 0. In some embodiments, the invention provides for compounds of Formula I. wherein $R^3$ is H. In some embodiments, the invention provides for compounds of Formula I. wherein $R^3$ is —$CH_2NR^8R^9$. In some embodiments, the invention provides for compounds of Formula I. wherein $R^1$ is independently F or Cl. In some embodiments, the invention provides for compounds of Formula I, wherein p can be 3.

In certain embodiments, there are provided compounds without limitation selected from the group consisting of:

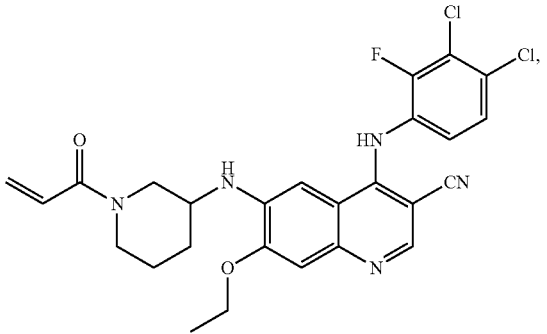

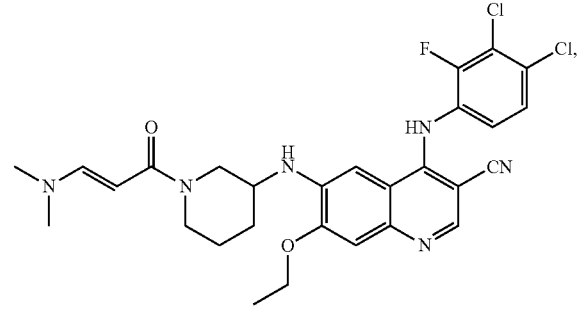

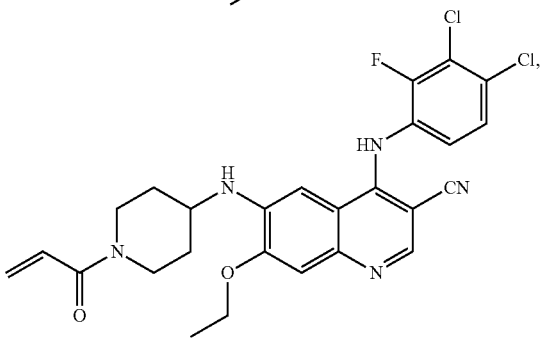

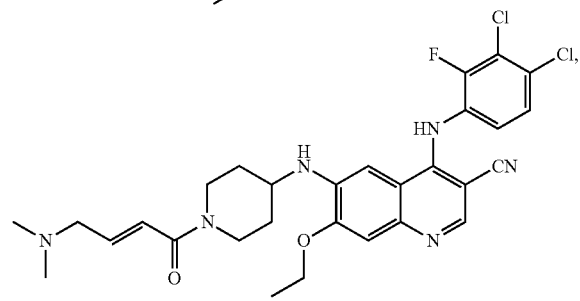

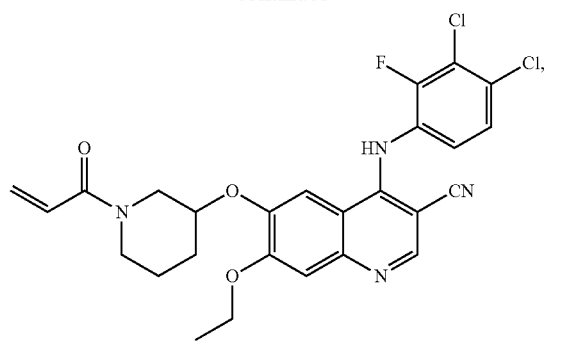

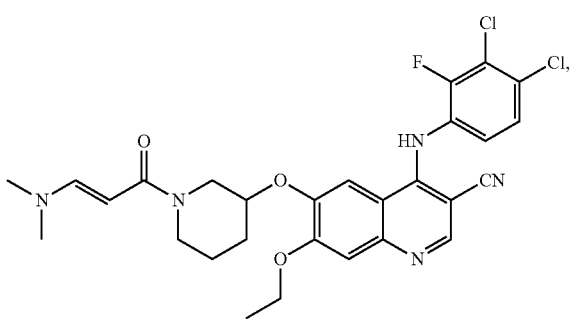

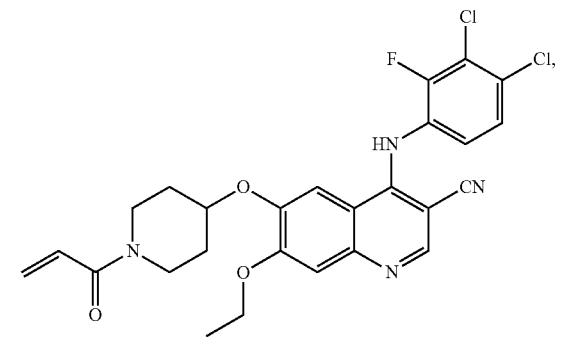

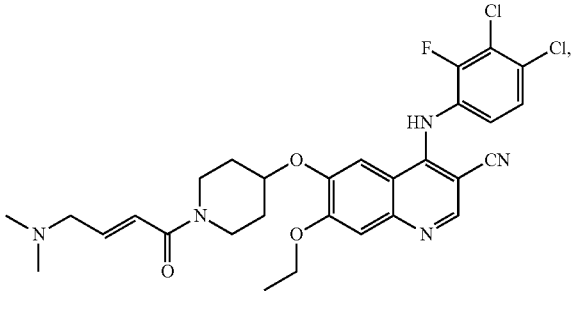

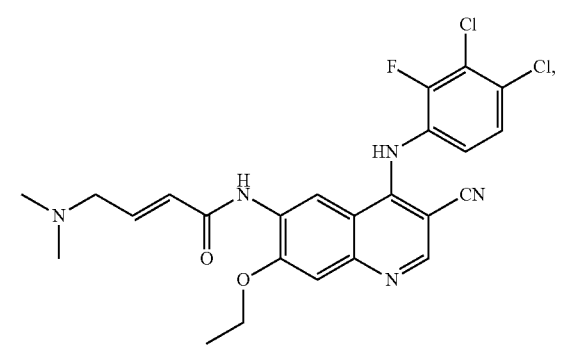

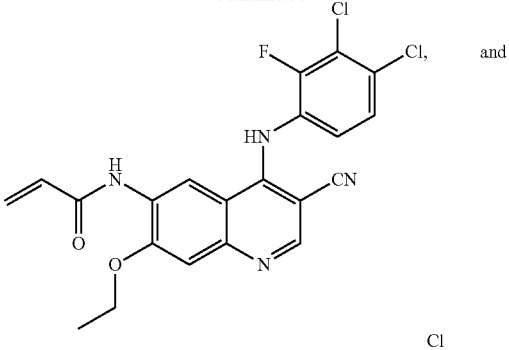

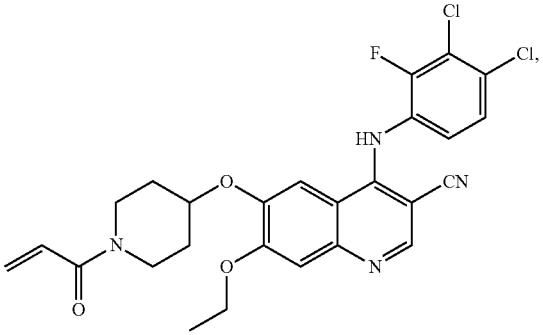

or a pharmaceutically acceptable salt, solvate, prodrug, or metabolite thereof.

In other embodiments, a pharmaceutical composition comprise compounds of Formula I and those disclosed above, or a pharmaceutically acceptable salt thereof; and a a pharmaceutically acceptable carrier.

In some embodiments, compounds of Formula I and those disclosed above, or a pharmaceutical composition thereof, can be for use as a medicament.

In other embodiments, compounds of Formula I and those disclosed above, or a pharmaceutical composition thereof, can be for use in the treatment of cancer.

In some embodiments, compounds of Formula I and those disclosed above, or a pharmaceutical composition thereof, can be for use in the treatment of a kinase mediated disease and/or condition.

In other embodiments, the compound of this invention is in the form of pharmaceutically acceptable salt. In some embodiments, the compound of this invention is in the form of a solvate. In other embodiments, the compound of this invention is in the form of a metabolite. In other embodiments, the compound of this invention is in the form of a prodrug. In some embodiments, the compound of this invention is an enantiomer. In other embodiments, the compound of this invention is a diastereomer. In another embodiment, the deuterium enrichment in compounds of this invention is at least about 1%.

In some embodiments, there are provided pharmaceutical compositions comprising a compound of the invention and a pharmaceutically acceptable carrier. In certain embodiments, the compositions are for the treatment of a disease regulated by a protein kinase. In certain embodiments, the compositions are for the prevention or the treatment of a hyper-proliferative disorder and/or angiogenesis disorder. In some embodiments, the pharmaceutical compositions further comprise an anti-neoplastic agent, an immunosuppressant, an immunostimulant, or combination thereof. In other embodiments, the pharmaceutical compositions are suitable for oral, parenteral, or intravenous administration.

In some embodiments, the present invention provides methods for regulating the kinase signaling transduction comprising administrating to a mammalian subject a therapeutically effective amount of any of the inventive compounds described herein.

In other embodiments, there are provided herein methods for treating or preventing a EGFR kinases mediated disorder, said method comprises administrating to a mammalian subject a therapeutically effective amount of any of the inventive compounds described herein.

In other embodiments, there are provided herein methods for treating neoplasia comprising administrating to a mammalian subject in need thereof, a therapeutically effective amount of any of the inventive compounds described herein. In certain embodiments, the neoplasia is selected from skin cancer, leukemias, colon carcinoma, renal cell carcinoma, gastrointestinal stromal cancer, solid tumor cancer, myeloma, breast cancer, pancreatic carcinoma, non-small cell lung cancer, non-Hodgkin's lymphoma, hepatocellular carcinoma, thyroid cancer, bladder cancer, colorectal cancer, and prostate cancer. In some embodiments, the methods further comprise administering one or more anti-cancer agents.

In other embodiments, there are provided methods for treating or preventing a hyper-proliferative and/or angiogenesis comprising administrating to a mammalian subject a therapeutically effective amount of any of the inventive compounds described herein.

Definitions

The following definitions should assist in understanding the invention described herein.

The term "alkyl" is intended to include straight, branched, and cyclic hydrocarbon groups, which contain only single carbon-carbon bonds and which may be unsubstituted or optionally substituted with one or more functional groups. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. The representative chain length of an alkyl group may be from 1 to 6 carbon atoms. $C_1$-$C_6$ alkyl is intended to include $C_1$, $C_2$, $C_3$, $C_4$, $C_5$ and $C_6$ alkyl groups. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^XR^Y$, wherein $R^X$ and $R^Y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring. Illustrative substituted alkyl group include, but are not limited to, fluoromethyl, difluoromethyl, trifluoromethyl, aminomethyl, aminoethyl, hydoxymethyl, methoxymethyl, 2-fluoroethyl, and 2-methoxyethyl, etc.

The term "alkoxy" refers to both an —O-(alkyl) and an —O-(unsubstituted cycloalkyl) group. $C_1$-$C_6$ alkoxy is intended to include $C_1$-$C_6$ alkyl groups, wherein $C_1$-$C_6$ alkyl is defined above. Representative examples include, but are not limited to, methoxy, ethoxy, propoxy, butoxy, cyclopropyloxy, cyclobutyloxy, cyclopentyloxy, cyclohexyloxy, and the like.

"Cycloalkyl" refers to a 3 to 8 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

"Aryl" refers to an all-carbon monocyclic or fused-ring polycyclic groups of 6 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —NRXRY, with RX and RY as defined above.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrazine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, 0-carboxy, sulfinyl, sulfonyl, O-carbamyl, N-carbamyl, O-thiocarbamyl, N-thiocarbamyl, C-amido, N-amido, amino and —NRXRY with RX and RY as defined above. A pharmaceutically acceptable heteroaryl is one that is sufficiently stable to be attached to a compound of the invention, formulated into a pharmaceutical composition and subsequently administered to a patient in need thereof.

"Heteroalicyclic" or "heterocycle" refers to a monocyclic or fused ring group having in the ring(s) of 3 to 12 ring atoms, in which one or two ring atoms are heteroatoms selected from N, O, and S(O)t, (where t is 0, 1 or 2), the remaining ring atoms being C. The rings may also have one or more double bonds. However, the rings do not have a completely conjugated □-electron system. Additionally, one or more of the ring atoms could be substituted by an oxo group. Examples of suitable saturated heteroalicyclic groups include, but are not limited to: tetrahydrofuran, tetrahydrothiophene, pyrrolidine, piperidine, morpholine, piperazine.

"Halogen" means fluorine, chlorine, bromine, and iodine. "Halo" means fluoro, chloro, bromo, and iodo, preferably fluorine or chlorine.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as deuterium and carbon such as $^{13}C$. Certain isotopically-labeled compounds of the invention, for example, those incorporating a radioactive isotope, are useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "comprising" is meant to be open-ended, including the indicated component(s), but not excluding other elements.

Deuterium (D or $^2H$) is a non-radioactive, stable isotope of hydrogen, the natural abundance of deuterium is 0.015%. A compound should be considered to be unnatural, if its level of deuterium has been enriched to be greater than the natural abundance level of 0.015%. In a compound of this invention, it is understood that the abundance of deuterium is substantially greater than the natural abundance of deuterium, which is 0.015%, when a particular position is designated as deuterium. A position designated as deuterium typically has a minimum isotopic enrichment factor of at least 3000 at each atom designated as deuterium in said compound. The concentration of naturally abundant stable hydrogen is small and immaterial compared to the degree of stable isotopic substitution of compounds of this invention.

The term "pharmaceutically acceptable" when used with reference to a compound of the invention is intended to refer to a form of the compound that is safe for administration to a subject. For example, a free base, a salt form, a solvate, a hydrate, a prodrug or derivative form of a compound of this invention, which has been approved for mammalian use, via oral ingestion or any other route of administration, by a governing authority or regulatory agency, such as the Food and Drug Administration (FDA) of the United States, is pharmaceutically acceptable.

Included in the compounds of Formula I are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of Formula I are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

The protection of functional groups by protecting groups, the protecting groups themselves, and their removal reactions (commonly referred to as "deprotection") are described, for example, in standard reference works, such as J. F. W. McOmie, *Protective Groups in Organic Chemistry*, Plenum Press, London and New York (1973), T. W. Greene and P. G. M. Wuts, *Protective Groups in Organic Synthesis*, Wiley, $3^{rd}$ edition, John Wiley and Sons (1999), E. Gross and J. Meienhofer, *The Peptides*, Volume 3, Academic Press, London and New York (1981).

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described below.

In synthesizing a compound of formula I according to a desired procedure, the steps in some embodiment, are performed in an order suitable to prepare the compound, including a procedure described herein or by an alternate order of steps described herein, and in one embodiment, be preceded, or followed, by additional protection/deprotection steps as necessary. The intermediates in some embodiments are isolated or carried on in situ, with or without purification. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, *Protective Groups in Organic Synthesis*, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Proton NMR Spectra

Unless otherwise indicated, all $^1$H NMR spectra were run on a Varian series Mercury 300, 400, 500 MHz instrument or a Bruker series 400, 500 MHz instrument. Where so characterized, all observed protons are reported as parts-per-million (ppm) downfield from tetramethylsilane (TMS) or other internal reference in the appropriate solvent indicated.

Synthesis of Compounds

The compounds of Formula I can be synthesized according to the procedures described in the following Schemes to those skilled in the art, wherein the substituents are as defined for Formula I above, except where further noted. The synthetic methods described below are merely exemplary, and the compounds of the invention may also be synthesized by alternate routes as appreciated by persons of ordinary skill in the art.

The synthesis of compounds of Formula I in the invention can be illustrated in the Schemes 1-3. According to Scheme 1, the reaction of commercial available starting materials 1 and 2 gives compound 3, which can be alkylated with compound 4 to afford compound 5.

Scheme 1

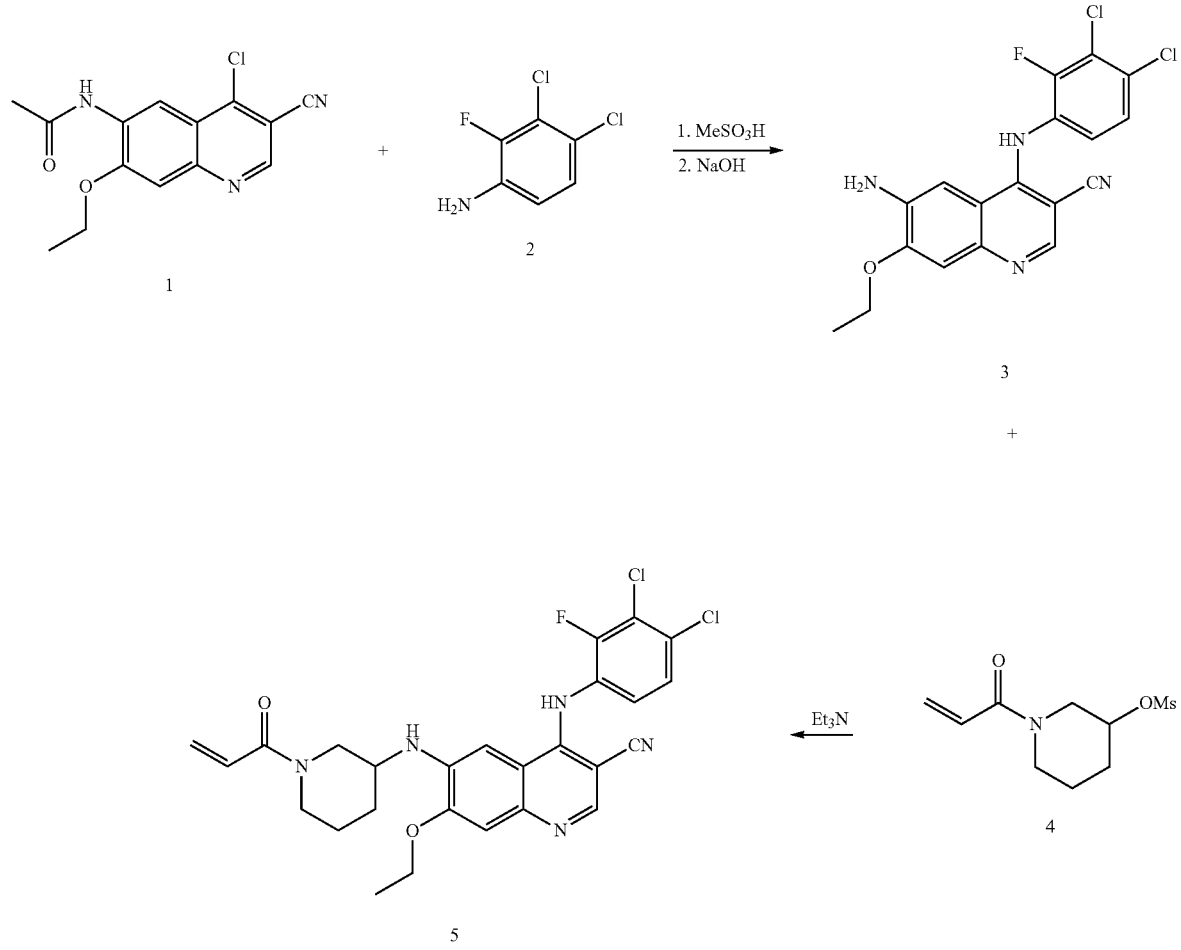

Scheme 2

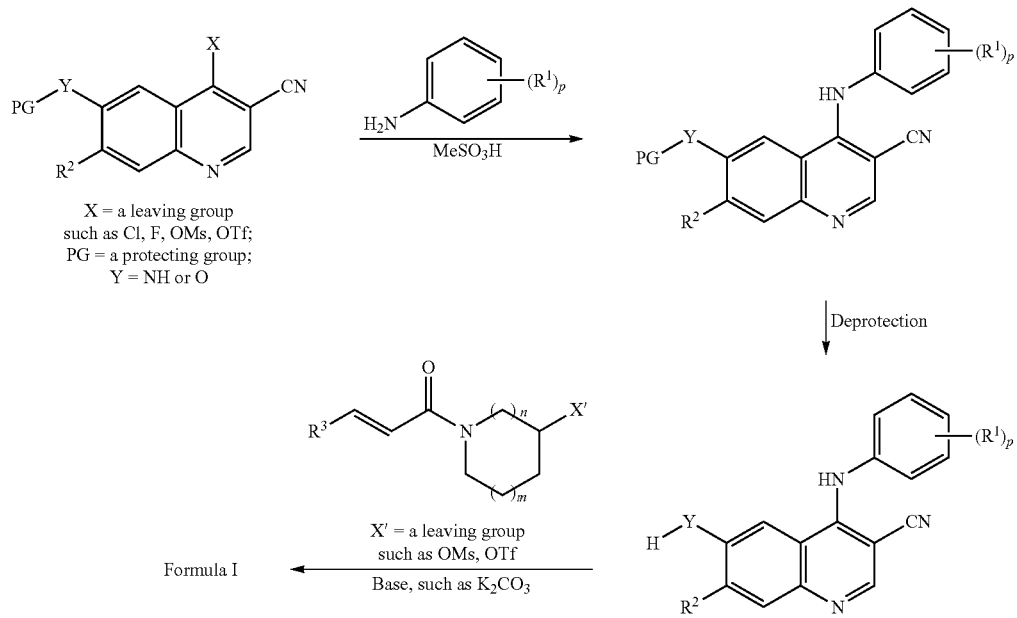

Similarly, compounds of Formula I can be made according to steps depicted in Scheme 2. The synthesis can begin with a nucleophilic substitution between a quinoline-3-carbonitrile bearing a leaving group at C-4 and a protected amine or hydroxyl group at C-6, and an aniline substituted or unsubstituted. Ensuing deprotection of the protecting group on the amine or hydroxyl group at C-6 of the quinoline can be followed by an alkylation reaction of displacing a leaving group X' on a pyrrolidine or piperidine or azepane to produce a compound of Formula I.

In addition, the amine or hydroxyl group at C-6 of the quinoline can be alkylated or acylated by other reagents as well as shown in Scheme 3.

Examples

Compound A was synthesized according to Scheme 4.

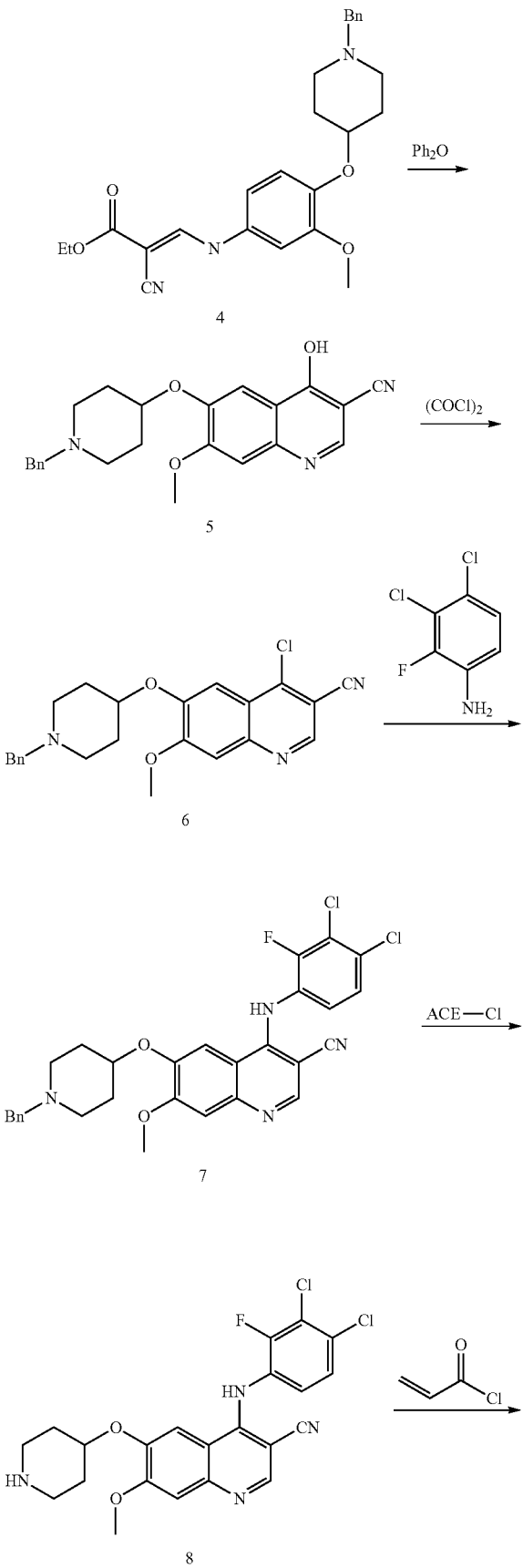

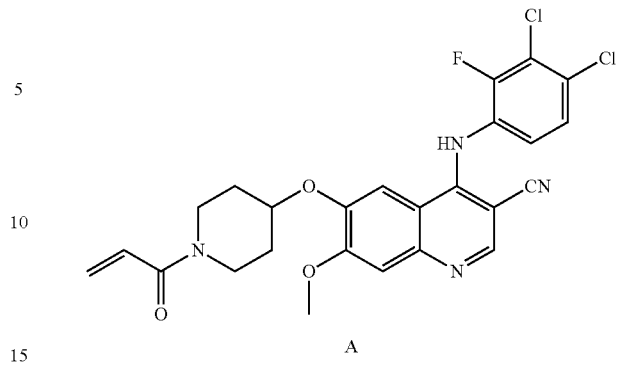

General: For the following synthesis of compound A, chemicals were purchased from SCRC, Sigma-Aldrich. ¹H NMR spectra were recorded on Bruker AVII 400. Generally, LCMS measurement were run on Agilent 1200 HPLC/6100 SQ System using the follow condition: Mobile Phase: A: Water (0.01% Ammonia) B: Acetonitrile; Gradient Phase: 5%-95% in 1.2 min; Flow rate: 1.8 mL/min; Column: XBridge; Oven temp: 50° C. ¹H-NMR spectra were recorded on a Varian Gemini 2000 using tetramethylsilane as an internal standard. Chemical shifts are expressed in δ (ppm) values, and coupling constants are expressed in hertz (Hz). The following abbreviations are used: s=singlet, d=doublet, m=multiplet, brs=broad singlet and dd=double-doublet. Mass spectra were recorded on JEOL JMS-DX303 or JEOL JMS-AX500 spectrometer. IR spectra were measured with SensIR ATR FT-IR.

Synthesis of Compound 2

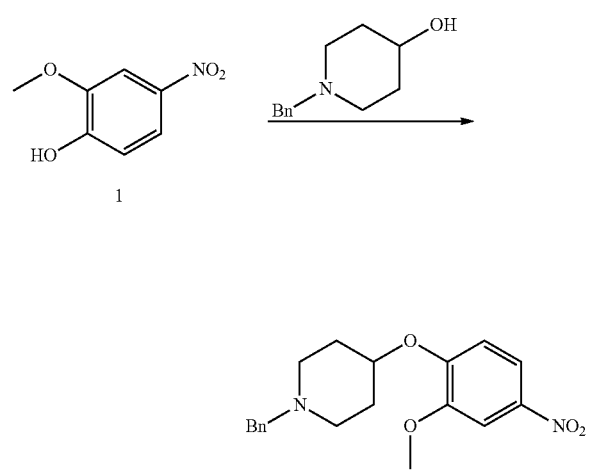

The compound 1 (5.1 g, 30 mmol), 1-benzylpiperidin-4-ol (6.88 g, 36 mmol) and PPh₃ (15.7 g, 60 mmol) were dissolved in THF (200 mL) at 0° C. The DIAD (9 g, 45 mmol) was added dropwise. It was stirred at room temperature (rt) for 16 h and then diluted with water. The mixture was extracted with EA, dried and concentrated. The residue was purified by FCC, eluting with 25% EA in PE to afford the compound 2 (10.0 g, 29 mmol, 97% yield) as an orange oil. LCMS: MS (M+H): 343, RT=1.45 min.

Synthesis of Compound 3

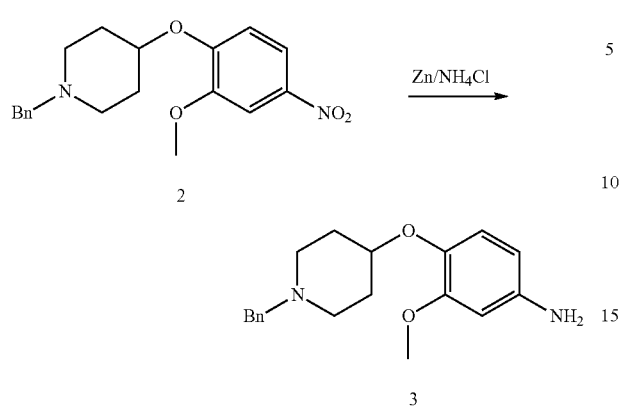

The compound 2 (10.0 g, 29 mmol) and NH₄Cl (38.5 g, 720 mmol) was dissolved in a solution of water (300 mL) and MeOH (100 mL) at 0° C. The zinc powder (9.45 g, 145 mmol) was added in portions. The mixture was stirred at rt for 16 h and then solids were settled without stirring for 1 h. The upper solution was decanted, and subsequently extracted with EA. Combined organic layers were dried and concentrated to dryness to afford Compound 3 (9.6 g, 29 mmol, 99% yield). LCMS: MS (M+H): 313, RT=1.03 min Synthesis of Compound 4

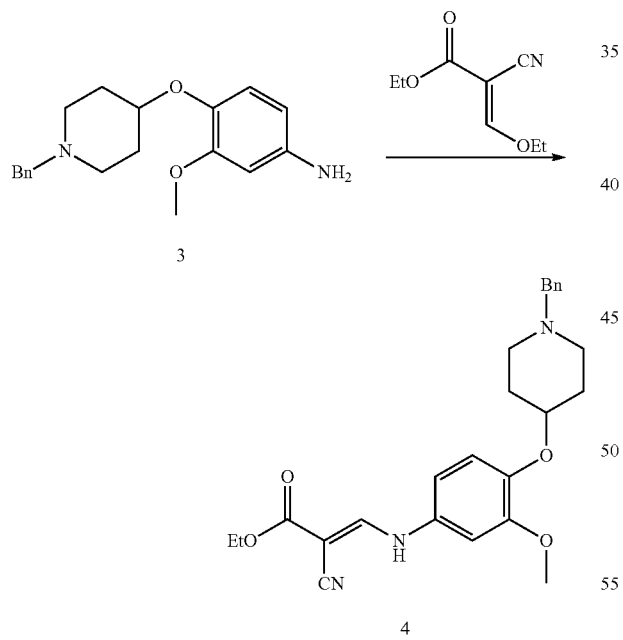

The compound 3 (10 g, 29 mmol) and (E)-ethyl 2-cyano-3-ethoxyacrylate (4.9 g, 29 mmol) were dissolved in toluenee (150 mL). The mixture was heated at 120° C. for 16 h. After cooling to rt, the reaction was concentrated to dryness. The residue was purified by FCC, eluting with 50% EA in PE to afford the compound 4 (4.65 g, 10.7 mmol, 37% yield) as a tan solid. LCMS: MS (M+H): 436, RT=1.46 & 1.54 min.

Synthesis of Compound 5

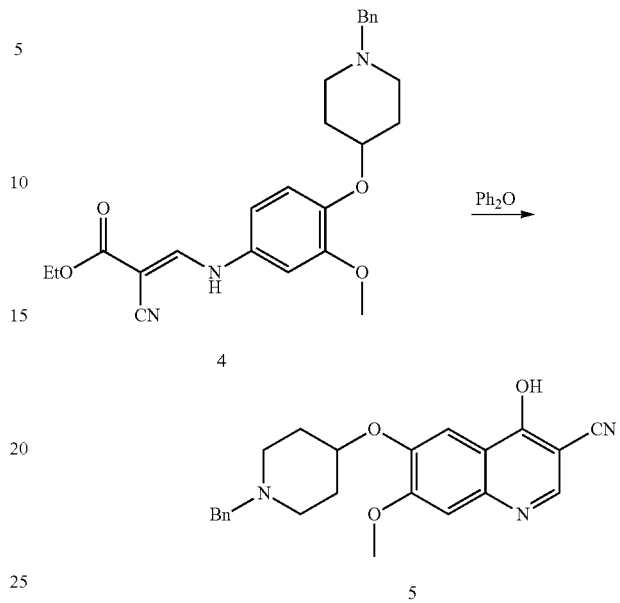

A mixture of Compound 4 (250 mg, 0.575 mmol) in Ph₂O (4 mL) was heated at 250° C. for 5 min under MW. The reaction mixture was absorbed on silica gel and purified by FCC, eluting with 10% MeOH in DCM to afford Compound 5 (100 mg, 0.25 mmol, 42% yield). The reaction was repeated 15 times to give compound 5 (660 mg, 1.70 mmol, total yield is 20%). LCMS: MS (M+H): 390, RT=1.18 min. $^1$H NMR (400 MHz, DMSO-d$_6$) δ 12.55 (brs, 1H), 8.59 (s, 1H), 7.48 (s, 1H), 7.41-7.22 (m, 5H), 7.02 (S, 1H), 4.48-4.46 (m, 1H), 3.88 (s, 3H), 3.65 (s, 2H), 2.70-2.68 (m, 2H), 2.33-2.27 (m, 2H), 1.97-1.74 (m, 2H), 1.70-1.61 (m, 2H).

Synthesis of Compound 6

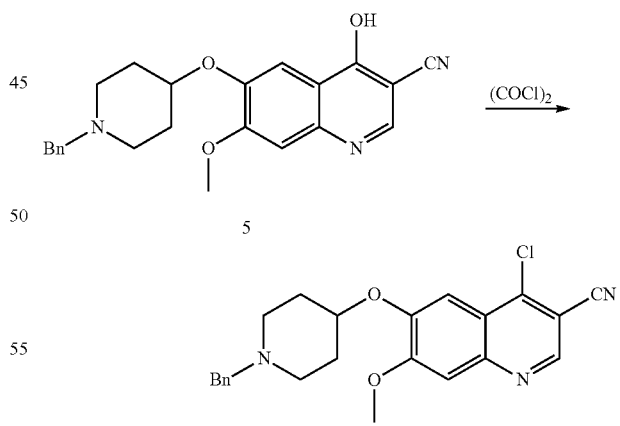

A stirred solution of Compound 5 (660 mg, 1.7 mmol) was dissolved in DCM (30 mL). The oxalyl chloride (1 mL, 7.9 mmol) was added and the solution was heated at 40° C. for 16 h. The reaction was concentrated to dryness to afford compound 6 (845 g, 1.7 mmol, 99% yield) as a HCl salt. LCMS: MS (M+H): 408, RT=1.49 min.

Synthesis of Compound 7

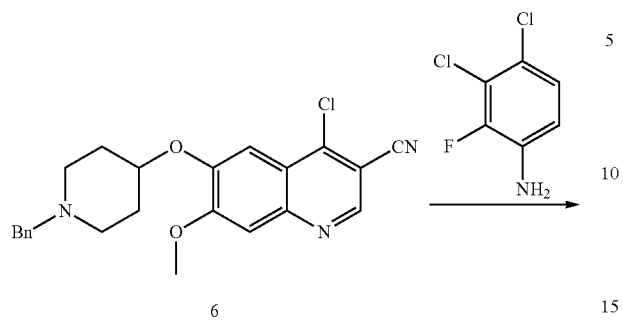

6

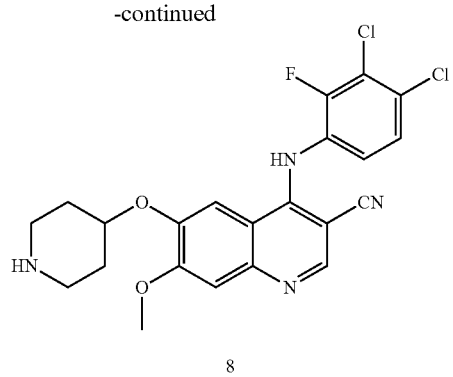

8

The compound 7 (360 mg, 0.65 mmol) was dissolved in DCE (20 mL). The 1-chloroethyl chloroformate (ACE-Cl, 186 mg, 1.3 mmol) was added and the reaction was heated at 80° C. for 1 h. The reaction was concentrated to dryness and the residue was re-dissolved in MeOH (20 mL). The solution was heated at 70° C. for 1 h. The mixture was concentrated to dryness and purified by FCC, eluting with 0-50% THF in DCM to afford compound 8 (180 mg, 0.39 mmol, 60% yield). LCMS: MS (M+H): 461, RT=1.38 min.

Synthesis of Compound A (4-(3,4-dichloro-2-fluoro-anilino)-7-methoxy-6-[(1-prop-2-enoyl-4-piperidyl)oxy]quinoline-3-carbonitrile)

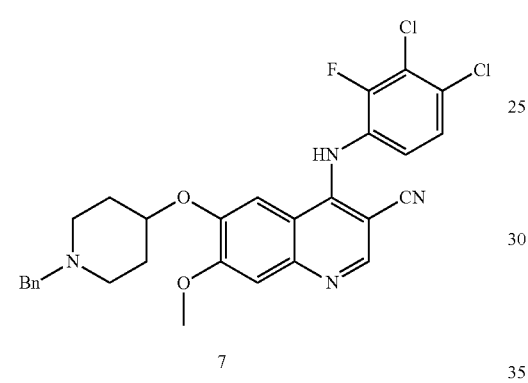

7

To a stirred solution of Compound 6 (845 mg, 1.7 mmol), 3,4-dichloro-2-fluorobenzenamine (367 mg, 2.04 mmol) and K$_2$CO$_3$ (704 mg, 5.1 mmol) in DMF (20 mL) was added 2-dicyclohexylphosphino-2',6'-diisopropoxybiphenyl (Ru-Phos, 80 mg, 0.17 mmol) and tris(dibenzylideneacetone)dipalladium(0) (Pd$_2$(dba)$_3$, 100 mg, 0.17 mmol). It was bubbled with N$_2$ three times and then heated at 100° C. for 16 h. After cooling to rt, the mixture was concentrated to remove DMF and the residue was deposited onto silica gel and eluted with 10% MeOH in DCM to afford compound 7 (360 mg, 0.65 mmol, 38% yield). LCMS: MS (M+H): 551, RT=1.80 min.

Synthesis of Compound 8

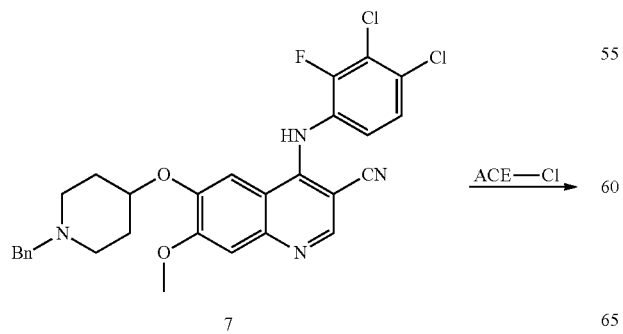

7

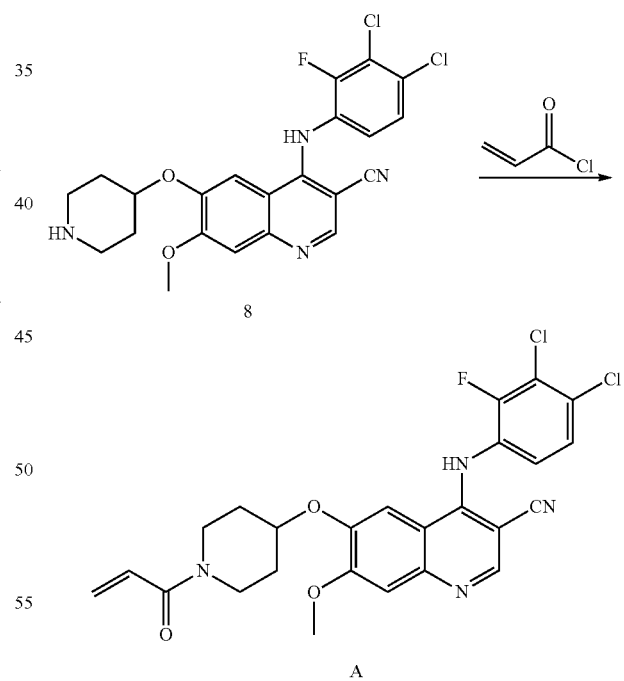

To a mixture of compound 8 (180 mg, 0.39 mmol) and saturated NaHCO$_3$ (5 mL) in THF (10 mL) was added with the acryloyl chloride (70 mg, 0.78 mmol). It was stirred at rt for 1 h. The reaction was extracted DCM, dried and concentrated to dryness. The residue was deposited onto silica gel and eluted with 0-50% THF in DCM to afford a yellow solid (55 mg). It was purified with prep-HPLC to afford compound A (17 mg, 0.033 mmol, 8% yield) as a white solid. LCMS: MS (M+H): 515, RT=1.52 min. $^1$H NMR (400 MHz, DMSO-$d_6$) δ 9.59 (s, 1H), 8.51 (s, 1H), 7.84 (s, 1H), 7.41-7.39 (m, 3H), 6.84-6.80 (m, I1H), 6.13-6.09 (m, 1H), 5.70-5.67 (m, 1H), 4.80-4.79 (m, 1H), 3.96 (s, 3H), 3.87-3.82 (m, 2H), 3.50-3.46 (m, 2H), 2.02-1.96 (m, 2H), 1.70-1.65 (m, 2H).

Indication

The present invention provides compounds which are capable of modulating one or more signal transduction pathways comprising, but not limited to EGFR-T790M kinase.

By the term "modulating," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Formulations and Method of Use

The amount of compound(s) which is/are administered and the dosage regimen for treating cancer with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Combinations

While the compounds of the invention can be dosed or administered as the sole active pharmaceutical agent, they can also be used in combination with one or more compounds of the invention or in conjunction with other agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula I is co-administered with a second therapeutic agent, wherein the compound of Formula I and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula I is initiated prior to, during, or after treatment with a second agent described herein, and continues until any time during treatment with the second agent or after termination of treatment with the second agent. It also includes treatments in which a compound of Formula I and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

The compounds of Formula I as well as combination therapies that include compounds of Formula I, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Specifically, the administration of compounds of the present invention in some embodiments are in conjunction with additional therapies known to those skilled in the art in the prevention or treatment of cancer.

Kinase Assays

As stated herein before, the compounds defined in the present invention possess anti-proliferation activity. These properties may be assessed, for example, using one or more of the procedures set out below.

In some assays, kinase-tagged T7 phage strains were prepared in an $E.\ coli$ host derived from the BL21 strain. $E.\ coli$ were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Kds (dissociation constants) were determined using a compound top concentration=10,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

Binding constants (Kds) were calculated with a standard dose-response curve using the Hill equation: Response=Background+(Signal−Background)/(1+ ($Kd^{Hill\ Slope}$/$Dose^{Hill\ Slope}$)). The Hill Slope was set to −1. Curves were fitted using a non-linear least square fit with the Levenberg-Marquardt algorithm.

The following Table A lists a compound representative of the invention and its inhibition activity in kinases assays.

TABLE A

Kinase Inhibition Results (Kd values)

| Compound | EGFR (D770_N771insNPG) Kd |
|---|---|
| Compound A | <0.5 nM |

Cell Proliferation Assays:

1. 5×10³ cells per well in 100 μl of medium were seeded in 96-well plate, while the medium here contained 5% FBS.

2. 24 hours later, 100 μl fresh medium was added with various concentrations of compounds into each well, while the medium here was free of FBS.

3. After the cells were treated with compounds for 72 hours, 20 μl 3-(4, 5-dimethylthiazolyl-2)-2,5-diphenyltetrazolium bromide (MTT, 5 mg/ml) was added into each well, and then the assay plate was incubated at 37° C. for 4 more hours.

4. The assay plate was centrifuged at 800 g for 10 min. The medium was aspirated, 150 μl DMSO was added into each well. The plate was gently shaken for 10 min.

5. The absorbance at 570 nm was measured on the plate reader.

6. The cell proliferation inhibition rate (IR) was calculated as: IR %=(WC−WT)/WC*100%, where WC is the cell weight of the control group and WT is the cell weight of treatment group.

The following Table B lists a compounds representative of the invention and its activity in cell assays in comparison to a control compound Erlotinib. After incubation of cells with a range of concentrations of the compound in the MTT assay (see above), an $IC_{50}$ value for the compound can be obtained in combination with cell viability of controls containing no compound. This $IC_{50}$ value is the concentration of compound where 50% of cells are viable.

TABLE B

Cell proliferation Assays ($IC_{50}$ values).

| Compound | Ba/F3 EGFR-D770_N771insSVD | Ba/F3 EGFR H773_V774insNPH |
|---|---|---|
| Compound A | 0.017 μM | 0.060 μM |
| Erlotinib | 2.46 μM | 3.65 μM |

What is claimed is:

1. A compound according to formula I:

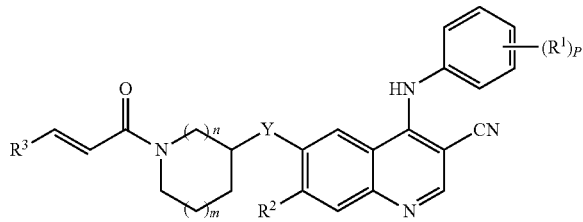

or a pharmaceutically acceptable salt, solvate, prodrug, stereoisomer, tautomer or metabolite thereof, wherein $R^1$ is independently hydrogen, $C_1$-$C_6$ alkyl, $C_1$-$C_6$ alkynyl, $C_1$-$C_6$ alkoxy, F, Cl, CN, or $CF_3$;

$R^2$ is hydrogen, $C_1$-$C_6$ alkyl, or $OR^4$;

$R^3$ is hydrogen, —$CH_2NR^8R^9$, or —$(CHR^{10})_tR^{11}$;

$R^4$ is $C_1$-$C_6$ alkyl, —$CR^6R^7(CR^6R^7)_qOR^5$, tetrahydrofuran-3-yl, —$(CH_2)_t$-morpholine, —$(CH_2)_t$-piperidine, or —$(CH_2)_t$-piperazine-N($C_1$-$C_3$ alkyl);

each $R^5$, $R^6$, and $R^7$ is independently hydrogen, $C_1$-$C_6$ alkyl, $C_6$-$C_{12}$ aryl, 5-12 membered heteroaryl, $C_3$-$C_{12}$ cycloalkyl or 3-12 membered heteroalicyclic; or any two of $R^5$, $R^6$, and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^5$, $R^6$, and $R^7$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;

$R^8$ and $R^9$ are independently hydrogen, $C_1$-$C_6$ alkyl, or $CR^6R^7(CR^6R^7)_qOR^5$;

each $R^{10}$ is independently hydrogen or $C_1$-$C_6$ alkyl;

$R^{11}$ is morpholine, piperidine, piperazine, piperazine-N ($C_1$-$C_6$ alkyl), or pyrrolidine, and each hydrogen in $R^{11}$ is optionally substituted by one or more $C_1$-$C_6$ alkyl, $C_1$-$C_6$ alkoxy, halogen, OH, $NH_2$, NH($C_1$-$C_6$ alkyl), or N($C_1$-$C_6$ alkyl)$_2$;

Y is Oxygen or Nitrogen;

each m is independently 0, or 1;

each n is independently 1, or 2;

each p is independently 0, 1, 2, 3, 4, or 5;

each t is independently 1, 2, or 3; and each q is independently 0, 1, 2, 3, or 4.

2. The compound of claim 1, wherein $R^2$ is $OR^4$.

3. The compound of claim 2, wherein $R^2$ is OEt or OMe.

4. The compound of claim 1, wherein n is 1 and m is 1.

5. The compound of claim 1, wherein n is 2 and m is 0.

6. The compound of claim 1, wherein $R^3$ is H.

7. The compound of claim 1, wherein $R^3$ is —$CH_2NR^8R^9$.

8. The compound of claim 1, wherein $R^1$ is independently F or Cl.

9. The compound of claim 1, wherein p is 3.

10. A compound selected from the group consisting of:
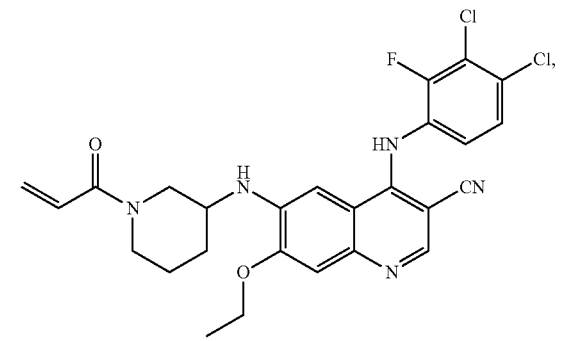
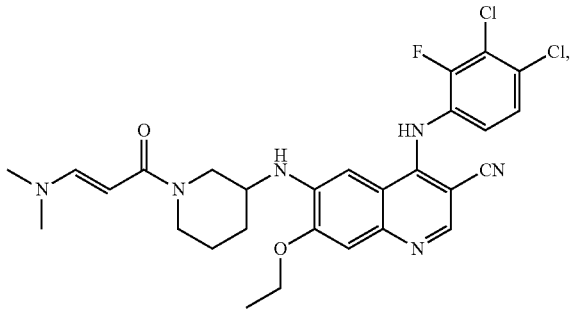
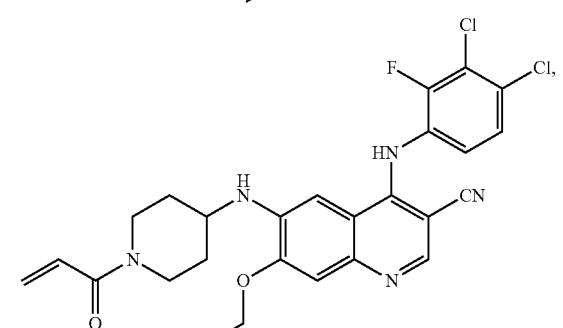
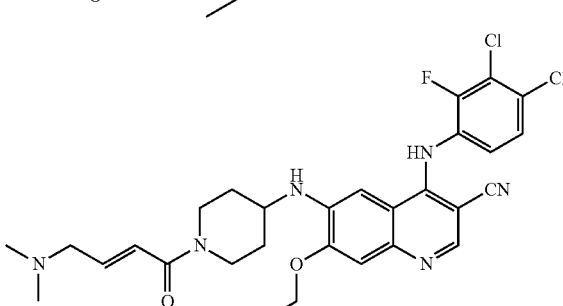
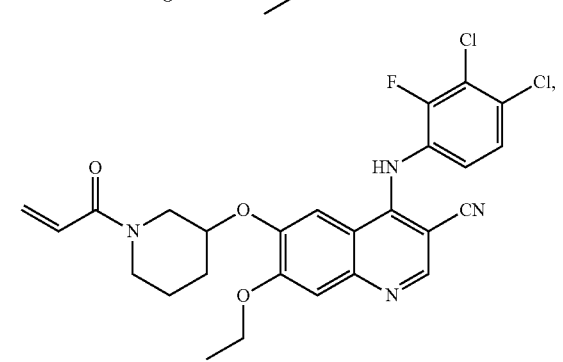
-continued
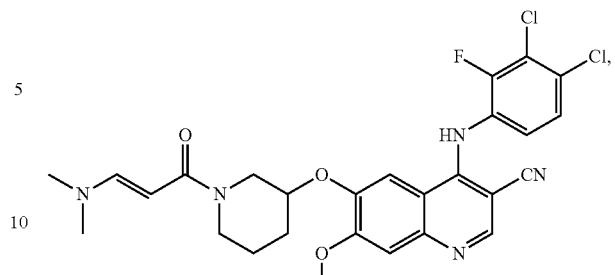
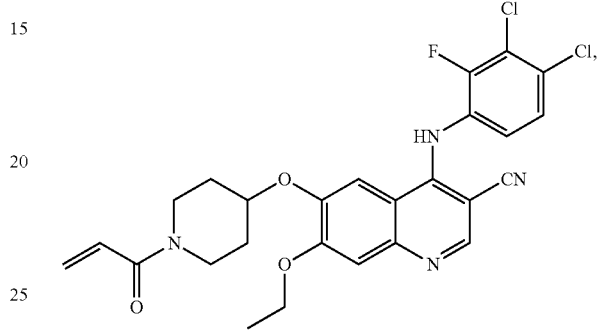
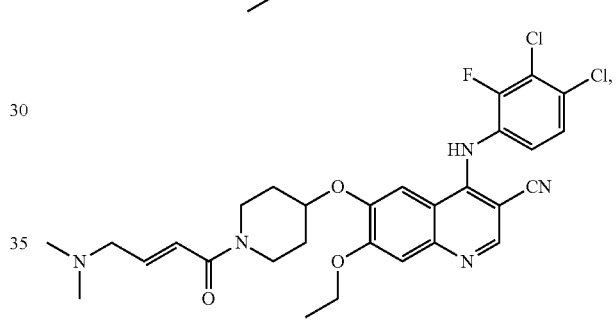
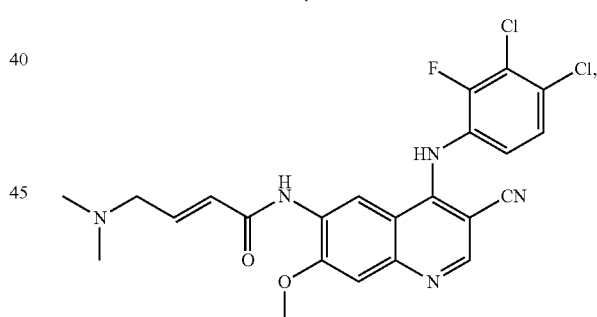
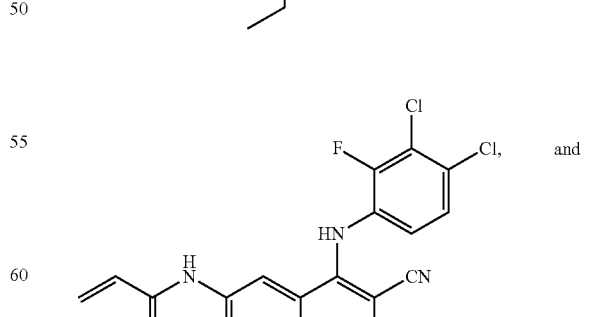
and
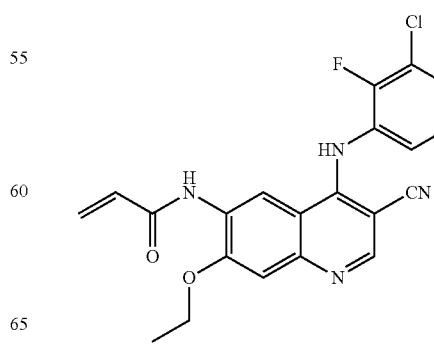

-continued

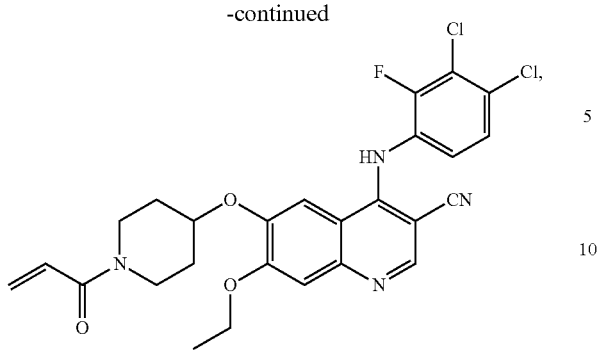

or a pharmaceutically acceptable salt, solvate, or prodrug thereof.

11. A pharmaceutical composition comprising a compound of claim 10, or a pharmaceutically acceptable salt thereof; and a pharmaceutically acceptable carrier.

12. The compound of claim 10, or a pharmaceutical composition thereof, for use as a medicament.

13. A pharmaceutical composition comprising a compound of claim 1, or a pharmaceutically acceptable salt thereof; and a pharmaceutically acceptable carrier.

14. The compound of claim 1, or a pharmaceutical composition thereof, for use as a medicament.

* * * * *